United States Patent [19]

Bhadra et al.

[11] Patent Number: 5,846,789

[45] Date of Patent: Dec. 8, 1998

[54] PROCESS FOR PREPARING NONTOXIC LIPOPOLYSACCHARIDES FROM ACIDIPHILIUM SPECIES

[75] Inventors: Ranjan Bhadra; Abhijit Nayak; Pataki Charan Bandyopadhyay; Sumanta Basu, all of Calcutta, India

[73] Assignee: Council of Scientific and Industrial Research, India

[21] Appl. No.: 763,182

[22] Filed: Dec. 10, 1996

[51] Int. Cl.⁶ .............................. C12P 19/04; A61K 39/02
[52] U.S. Cl. .................... 435/101; 435/822; 424/234.1
[58] Field of Search ........................... 435/101; 424/234.1

[56] References Cited

U.S. PATENT DOCUMENTS 4,230,801  10/1980  Gutnick et al. ........................ 435/101
5,382,428   1/1995  Livingston-Wheeler et al. ... 424/234.1

OTHER PUBLICATIONS

Basu et al., "Lipopolysaccharides of the acidophilic heterotrophic bacteria *Acidiphilium cryptum* and *Acidiphilium symbioticum*", Microbiology Letters 118 : 65–70 (1994).

*Primary Examiner*—Sandra E. Saucier
*Attorney, Agent, or Firm*—Schweitzer Cornman Gross & Bondell LLP

[57] ABSTRACT

A process for preparing a nontoxic lipopolysaccharide, which comprises (i) cultivating in a culture medium bacteria of the genus Acidiphilium having accession No. MTCC 1979, (ii) separating the culture bacteria, and repeatedly washing the separated bacteria, (iii) extracting the washed bacteria with a lipophilic solvent, (iv) cooling the extract and repeatedly centrifuging the cooled material, (v) dialyzing the supernatant resulting from said centrifuging, (vi) lyophilizing the dialyzed material, (vii) precipitating the lipopolysaccharide by treating the lyophilized material with a polar solvent, and (viii) drying the precipitated polyliposaccharide.

12 Claims, No Drawings

PROCESS FOR PREPARING NONTOXIC LIPOPOLYSACCHARIDES FROM ACIDIPHILIUM SPECIES

FIELD OF THE INVENTION

This invention relates to a process for the preparation of a new, potent, nontoxic liposaccharide (LPS) useful for preventing endotoxemia or sepsis.

BACKGROUND

The two-layered and asymmetrically organized membrane, the so called outer membrane of Gram negative bacteria such as *Escherichia coli* and *Salmonella entericia* is comprised of certain kinds of proteins and a class macro-amphiphiles. The LPS are the dominating constituents. The viability of these protein bacteria is a protein solely dependent on array of LPS on the outer membrane of the cell. One bacterial cell contains an approximately $3.6 \times 10^6$ LPS molecules occupying an area of 4.9 micro square meters. It appears that its interaction is easy with the target.

Upon infection with a Gram negative pathogen, the LPS released in the circulation mediates various physiological and pathophysiological interaction with a host particularly a human loop leading to the endangerment of its survival. The pathophysiological disorders caused by LPS of Gram negative bacterial infection in humans include fever of about 38.6° C. tachycardia of greater than 90 beats/min, lachypnea of a respiratory rate greater than 20 breaths/min, acidosis of pH 7.3, and arterial hypoxemia of about of 75 mm Hg. In the United States alone every year about 500,000 people suffer sepsis and about 175,000 of these die. In India the statistics are even worse because of the larger population and septicemia occurs at a higher rate with greater impact on the mortality rate. Usually patients in hospitals or in intensive care units having an incidence of septic shock die within about 72 hours of diagnosis.

Amongst the mediators that are produced by LPS action on reticuloendothelial cells are Tumor Necrosis Factor (TNF) and interleukin-1 (IL 1) in addition to interleukin-6 and -8. However TNF α IL-1 are critical factors for septicemia.

Understanding the greater impact of sepsis on human population, according to an analytical report by Oppenheimer & Co. Inc. of New York City, the market for successful antisepsis drugs could be about $500 million per year. The burgeoning market represent a major source of income for the 20 or so drug companies currently working on developing an antisepsis drug. However this is not a simple task.

Starting in mid 1980's three companies Centocor Xoma, and Chiron of Emeryville, Calif. developed a monoclonal antibody to lipid-A, the toxic component of endotoxin that plays a key role in generating sepsis. By binding to receptors on the monocytes and macrophages, the lipid-A of endotoxin triggers the release of powerful mediators known as cytokines. The purpose to use antibodies to collect excess Lipid-A before it can cause sepsis was relied on by Xoma and Centocor in the clinical trials of their product candidates, but without any success. However Ribiimmunochem in Hamilton, Mont. developed a benign form of Lipid-A which tolerates the host and the immune system no longer becomes overstimulated when there is infection with Gram negative and positive bacteria. Another approach for antiendotoxin activity is the use of a bactericidal/permeability increasing protein (RPI) a self protein that is present in white blood cells and binds to endotoxin and thereby mimics the body's own action. Incyte Pharmaceuticals of Palo Alto, Calif. developed RPI. This drug showed good results in mice. Due to a shift in the pathogens causing sepsis such as Gram positive bacteria and fungi, the focus is now directed toward immune mediators such as TNF and IL-1.

Antril (receptor antagonist of IL-1) from Synergen, is a protein produced by monocytes and helps in counteracting the effect of IL-1 by binding to its receptors on neutrophils. This has shown good results in, already ill patients. Several companies such as Chiron, and Hoffmann-la-Roche had found encouraging results using TNF-binding antibodies and is now testing them in humans.

However, the anti TNF receptor approach was not successful because it was reported to increase mortality in sepsis patients. The anticytokine approach is strongly defended by a number of scientists, but others complain that controls triggering of only one chemical reaction at a time. Nevertheless, controlling one factor increases the effects of others. Therefore, if TNF is blocked there is enough redundancy in the immune system that IL-1 level will probably go up.

Therefore, Erickson a cell biologist at the University of California points out that a successful therapy against sepsis requires a cocktail of agents that works against both TNF and IL-1. EntreMed Inc. of Rockville, Md. has used on "antisepsis vaccine" to get patients to increase their own immune responses. The "vaccine" contains Lipid-A seated in vesicles made of lipids and cholesterol and is in development. Therefore, a possible approach in the direction of "antisepsis vaccine" is attempted with a naturally occurring nontoxic LPS which is immunologically cross reactive with *E. coli* LPS but would show no lethality at a very high dose. On the contrary, it prevents lethal shock induced by Gram negative toxic LPS or endotoxin.

In the state of art there are various standard extraction and dialysis processes known for producing LPS.

Extraction with Trichloroacetic Acid.

Extraction of the cell with trichloroacetic acid (TCA) is the historically initial method for isolation of endotoxin. This a highly immunogenic LPS protein-phospholipid complex.

Cells suspended in five times their weight in ice cold water, are treated with an equal volume of 0.5N TCA at 4° C. for 3 hours. The suspension is centrifuged and the supernatants are neutralized with dilute sodium hydroxide, and the complex is precipitated with two volumes of water, then dialyzed, centrifuged to remove the cell debris, and then lyophilized.

Extraction with Ethylene Glycol

Diethylene glycol selectively extracts free polysaccharide and/or the whole O-antigen complex from cells. The extraction conditions are very mild and the risk of degradation or modification of the extracted material is low. Acetone-dried cells are extracted with 10 parts of freshly distilled diethylene glycol by shaking for several hours each day at room temperature. The extract is filtered, dialyzed and concentrated. The O-antigen complex is finally precipitated by addition of acetone at −10° C. Further purification is carried out by fractionation with a 1%, saturated aqueous ammonium sulfonate solution. The procedure is lengthy and the yield is low.

Extraction with Hot Phenol

The two aforementioned extraction method are useful mostly is the isolation procedure developed by Westphal and Jann in 1965. The extracted material is slightly contaminated with protein. The method works well for extraction of S and R type of LPS, although it is often not complete for R mutants.

Extraction with Dimethyl Sulphoxide (DMSO)

At higher temperature such as above 60° C. DMSO extracts the LPS with protein. LPS free of protein can be obtained from this extract by O-acetylation, and subsequently purifying with chloroform. The product is finally deacylated with a 2% solution of DMSO in acetone at room temperature. Part of ester-linked fatty acids are removed from lipid-A during the deacylation.

Extraction with Phenol Chloroform Petroleum Ether (PCP)

The phenol with water extraction method often does not quantitatively extract the more hydrophobic endotoxin present in R mutants. In that case dried bacteria are homogenized in the mixture of liquid phenol-chloroform petroleum ether (2:5:8 v/v/v), then centrifuged, and the supernatant is collected. Chloroform and petroleum ether are removed by evaporation from the supernatant. Water is dropwise added to precipitate the LPS from the remaining phenol. The precipitate is centrifuged followed by washing with petroleum ether and acetone with further purification by ultracentrifugation at 105,000 r.p.m. for 4 hrs.

Electrodialysis

Isolated endotoxin from both S and R forms are usually associated with a number of mono and divalent cations such as $Na^+$, $K^+$ $Mg^{++}$, $Ca^{++}$, and some polyamines such as spermidine and spermine. These cations have strong influence on solubility and aggregation of LPS. Electrodialysis of LPS enables its conversion to the salt form by neutralization with respective basis. Triethylamine salt form of LPS is highly water soluble. This salt is not sedimented during ultracentrifugation and shows modified biological activities. Not neutralized electrodialyzed LPS preparations are not stable for sufficiently long time periods, resulting in deterioration on storage due to autolysis.

The lethal dose of toxic LPS of *E. coli* 80 microgram/mouse and the lethal dose of nontoxic LPS of the present invention in non-galactosamine sensitized mice, is as high as 3 mg/mouse. Other reported to be nontoxic LPS such as those of *R. spheroids* and *R. capsulatus* were pyrogenic and lethal at the same doses used in testing the nontoxic LPS made by the present invention. Some companies such as Sandoz are actively pursuing the preparation of a synthetic Lipid-A with least toxicity having antagonistic activity for toxic LPS.

DESCRIPTION OF THE INVENTION

The main objective of the present invention is to provide a process for the preparation of a new lipopolysaccharide from a new bacterial strain from the Acidiphillium genus isolated from the soil in the areas of copper mines.

Another objective of the invention is to provide a process for the preparation of a new lipopolysaccharide as a intervening agent for toxic LPS action culminating in endotoxemia without itself being toxic.

Accordingly, the present invention provides a process for the preparation of a new nontoxic lipopolysaccharide, useful for endotoxin shock which comprises i) culturing a bacteria of the genus Acidophilium having the accession No. ATCC 55963, 10801 University Boulevard, Manasses, Va. 20110-2209 in a conventional nutrient medium under standard conditions such as a culture medium containing a hexose such as glucose, a galactose as a carbon source, and a rich nitrogen source such as a yeast extract, ammonium sulfate, (ii) separating the bacteria and repeatedly washing the separated bacteria with the same culture medium except that the medium does not contain any carbon and nitrogen source, (iii) extracting the bacteria with a lipophilic solvent at temperature of from 70° C. to 90° C., (iv) cooling the resultant extract and centrifuging it repeatedly, (v) dialyzing the supernatant resulting from said repeated centrifuging, (vi) lyophilizing the dialyzed material, (vii) treating the lyophilized material with a polar solvent to precipitate the lipopolysaccharide, and (viii) filtering and drying the precipitated lipopolysaccharide.

The lipopolysaccharide prepared in accordance with the present invention is 150–200 times less toxic than the known nontoxic LPS, and the lipopolysaccharide prepared by the present invention is 2 million times less toxic than *E. coli* LPS, and 150–200 times less toxic than *R. spheorides*. The present nontoxic LPS is useful as preventive agent against endotoxemia.

The bacterial culture can be grown in a synthetic culture medium enriched with glucose and yeast extract, and incubated as low as 30° C. to 39° C. in 72–120 hours.

The cells are harvested after cell growth by centrifugation at 4,000 to 10,000 r.p.m. from 30 to 100 minutes, followed by washing with the same medium as was employed for the growth, but without containing any glucose and yeast extract.

Bacterial cells are then treated with hot lipophilic solvent such as an aromatic phenol or a maximum $C_4$ aliphatic alkanol, and water. The above mixture was then vigorously stirred 60 to 120 minutes. Then the mixture is cooled on ice to 2° C. to 12° C. The mixture was then centrifuged at from 4,000 to 10,000 r.p.m. for 15 to 30 minutes.

The above procedure is repeated three times. The total supernatant was exhaustively dialyzed 2 to 5 days. Then the material was lyophilized and subjected to ultracentrifugation at from to 105,000 to 170,000 r.p.m. for from 4 to 6 hours at a temperature of from 7° C. to 4° C. as a 1.5 to 7.5% solution. The water used in the entire process was entirely pyrogen free and was carefully guarded from any contamination from the environment. Centrifugation was repeated to obtain nearly pure LPS. This was then treated with a polar solvent like ethanol. The precipitate was collected by centrifugation at 8,500 to 14,000 r.p.m. for 20 to 45 minutes and lyophilized for storage in refrigerator.

The nontoxic LPS (NTLPS) prepared in accordance with this invention is an unique kind of LPS from a new strain of Acidiphillium bacterium which is a new source of a NTLPS. The lipopolysaccharide which prepared by the process of the present invention is a bioactive substance and useful for preventing pathophysiological interaction with endotoxin of Gram negative bacteria including human pathogens. This lipopolysaccharide is prepared in accordance with the present invention from a new bacterium belonging to the genus Acidiphilium and having accession No. MTCC 1979 and deposited in the National Culture Centre IMTFC, in Chandigargh, India. The accession No. refers to that number in this depository.

Usually the basic structure of Lipid-A has 4 to 8 acyl chains with varying degrees of chain length. In a comparative study of the relation between structure and function of LPS various modification forms of *E. coli* LPS have been illustrated and their bioactivity showed some striking features. More β-hydroxylation and a lower number of fatty acyl chains result in drastically reduced bioactivity by a factor of $10^7$. The nontoxic LPS prepared by the process of this invention has a higher proportion of β-hydroxylated fatty acid acyl chains, namely myristic acid chains which possibly account for its nontoxicity, though the NTLPS is immunologically cross reactive with *E. coli*.

The composition of this nontoxic LPS i.e. the GR18h LPS from the MTCC 1979 strain, is:

|   |   | % OF TOTAL |
|---|---|---|
| A. | SUGAR | |
|   | Galactose | 77.3 |
|   | Glucose | 9.06 |
|   | Mannose | 3.4 |
|   | d-l Heptose | 1.2 |
| B. | FATTY ACID | |
|   | R-OH-C14:0 | 58.3 |
|   | C16:0 | 11.95 |
|   | C12:0 | 3.75 |
|   | C16:1 | 14.63 |

The nontoxic LPS of the present invention is composed of electrophoretically low molecular weight components as electrophoretically compared to *E. Coli* LPS. The high degree of its immunological crossreactivity with *E. Coli* LPS suggests it as structurally very closely related material to *E. Coli* LPS.

The invention is illustrated in greater detail in the following examples.

EXAMPLE 1

A strain of the MTCC 1979 bacterium was made by culturing, harvesting and weighing at wet weight of 70 g., and a dry/wet weight 4 g. under the following conditions:

| POSSES PARAMETERS | CONDITIONS |
|---|---|
| Volume of culture for 2 days | 5 l |
| Weight of bacterial cell | 4 g. (dry wt.) |
| Volume of pyrogen free water | 70 ml |
| Volume of distilled phenol | 70 ml |
| Temperature | 68° C. |
| Duration of stirring | 30 minutes |
| Speed of centrifugation | 105,000 r.p.m. |
| Duration of centrifugation | 4 hours |
| Crude LPS obtained | 100 mg |
| Purified LPS obtained | 75 mg. |

EXAMPLE 2

| Volume of culture (for 2 days) | 5 l |
|---|---|
| Weight of bacteria cell (with higher concentration of glucose) | 6 g. (dry wt.) (2 g/l) |
| Volume of pyrogen free water | 70 ml |
| Temperature | 68° C. |
| Duration of stirring | 30 minutes |
| Speed of centrifugation | 105,000 g |
| Crude LPS obtained | 130 mg |
| Purified LPS obtained | 105 mg |

EXAMPLE 3

| Volume of culture (2 days) | 2.5 l |
|---|---|
| Weight of bacteria cell | 2 g |
| Volume of pyrogen free water | 35 ml |
| Volume of distilled phenol | 35 ml |
| Temperature of extraction | 75° C. |
| Duration of centrifugation | 30 minutes |
| Speed of centrifugation | 105,.00 r.p.m. |
| Duration of centrifugation | 4 hours |
| Crude LPS obtained | 52 mg |
| Purified LPS obtained | 38 mg |

Experimental evidence of the nontoxic nature is derived from the lipopolysaccharide prepared by the process of the present invention on 2 groups of mice, each group having 5 animals. The mice were subjected to survival testing upon administration of the lipopolysaccharide prepared by this invention and another, the toxic variety, namely of *E. coli*.

Only normal saline solution was injected into one group, and LPS was injected into the other group. No death was observed in 5 days. On the 5th day the toxic LPS was injected in the mice of both groups. The mice of the saline treated group died within 72 hours, but the nontoxic lipopolysaccharide-treated mice all survived without any mortality. All injections were given after mildly anasthesizing to the mice.

We claim:

1. A process for preparing a nontoxic lipopolysaccharide, the process comprising:
   (i) cultivating in a culture medium bacteria of the genus Acidiphilium having accession No. ATCC 55963,
   (ii) separating the cultured bacteria, and repeatedly washing the separated bacteria,
   (iii) extracting the washed bacteria with a lipophilic solvent at an elevated temperature,
   (iv) cooling the extract and repeatedly centrifuging the cooled material,
   (v) dialyzing the supernatant resulting from said centrifuging,
   (vi) lyophilizing the dialyzed material,
   (vii) precipitating the lipopolysaccharide by treating the lyophilized material with a polar solvent, and
   (viii) drying the precipitated lipopolysaccharide.

2. The process of claim 1, wherein said culture medium contains a hexose as a carbon source, a nitrogen source, and a salt as a mineral source.

3. The process of claim 2, wherein said hexose is one or more of glucose, and galactose.

4. The process of claim 2, wherein said nitrogen source is one or more of yeast extract, and ammonium sulfate.

5. The process of claim 2, wherein said mineral source is one or more of magnesium dihydrogen phosphate, and potassium chloride.

6. The process of claim 2, wherein said repeated washing of the separated bacteria is carried out with the composition of the culture medium, except for its carbon source and nitrogen source content.

7. The process of claim 1, wherein said extracting is carried out at a temperature between 70° C. and 90° C.

8. The process of claim 1, wherein said separating of the bacteria is carried out by centrifuging, sharple centrifuging, membrane filtration, or prolonged gravitational precipitation.

9. The process of claim 8, wherein said centrifuging is carried out at an r.p.m. from 4,000 to 10,000.

10. The process of claim 1, wherein said lipophilic solvent is one or more of phenol, butanol, and water.

11. The process of claim 1, wherein said lyophilization is carried out by freeze drying the dialyzed material.

12. The process of claim 1, wherein said polar solvent is a $C_{1-4}$ aliphatic alkanol.

* * * * *